United States Patent
Vollkommer et al.

(10) Patent No.: US 6,545,427 B1
(45) Date of Patent: Apr. 8, 2003

(54) DISCHARGE LAMP HAVING AN IMPROVED TEMPERATURE HOMOGENEITY

(75) Inventors: Frank Vollkommer, Buchendorf (DE); Lothar Hitzschke, Munich (DE)

(73) Assignee: Patent-Treuhand-Gesellschaft für elektrische Glühlampen mbH, Munich (DE)

( * ) Notice: Subject to any disclaimer, the term of this patent is extended or adjusted under 35 U.S.C. 154(b) by 0 days.

(21) Appl. No.: 09/889,371

(22) PCT Filed: Oct. 6, 2000

(86) PCT No.: PCT/DE00/03519

§ 371 (c)(1), (2), (4) Date: Sep. 7, 2001

(87) PCT Pub. No.: WO01/37318

PCT Pub. Date: May 25, 2001

(30) Foreign Application Priority Data

Nov. 16, 1999 (DE) .......................... 199 55 108

(51) Int. Cl.[7] .............................................. H05B 41/16
(52) U.S. Cl. ...................... 315/246; 315/260; 313/607; 313/634; 313/15; 313/24
(58) Field of Search ......................... 315/246, 326, 315/334, 339, 260, 291; 313/15, 619, 23, 24, 260, 484, 491, 494, 514, 518, 607, 634; 250/493.1

(56) References Cited

U.S. PATENT DOCUMENTS

| | | | |
|---|---|---|---|
| 5,315,211 A | | 5/1994 | Ditlevsen et al. |
| 5,514,934 A | * | 5/1996 | Matsumoto et al. ........... 313/1 |
| 5,604,410 A | * | 2/1997 | Vollkommer et al. ....... 313/607 |
| 5,973,453 A | * | 10/1999 | Van Vliet et al. ........... 313/606 |
| 6,049,086 A | * | 4/2000 | Foggiato et al. ........ 250/504 R |
| 6,067,155 A | * | 8/2000 | Vollkommer et al. ....... 313/234 |
| 6,246,171 B1 | * | 6/2001 | Vollkommer et al. ....... 313/491 |

FOREIGN PATENT DOCUMENTS

| | | |
|---|---|---|
| DE | 198 11 520 C | 8/1999 |
| JP | 01 014 857 A | 1/1989 |
| WO | 98 432 76 A | 10/1998 |

* cited by examiner

Primary Examiner—Haissa Philogene
(74) Attorney, Agent, or Firm—Cohen, Pontani, Lieberman & Pavane

(57) ABSTRACT

A discharge lamp for dielectrically impeded discharges, having a discharge vessel filled with a discharge medium and having discharge electrodes which are at least partly separated from the discharge medium by a dielectric layer, wherein the discharge vessel is elongated at least in a longitudinal direction, characterized by a thermal device for controlling the heat transport into and out of the lamp nonhomogeneously in the longitudinal direction, which is designed such that in operation, the temperature in the lamp is made homogeneous in the longitudinal direction.

16 Claims, 6 Drawing Sheets

DISCHARGE LAMP HAVING AN IMPROVED TEMPERATURE HOMOGENEITY

This application is a U.S. National Phase Application under 35 USC 371 of International Application PCT/DE00/03519 (not published in English) filed Oct. 6, 2000.

FIELD OF THE INVENTION

The invention relates to a discharge lamp designed for dielectrically impeded discharges. Such a discharge lamp typically has a discharge vessel, which contains the discharge medium, conventionally xenon, or more generally a gas mixture with a noble gas. For ignition and maintenance of the discharges, electrodes are provided; discharge lamps designed for dielectrically impeded discharges are distinguished in that at least the electrodes designed as anodes are separated from the discharge medium by a dielectric layer, which can also be a wall of the discharge vessel. It is also possible for all the electrodes to be dielectrically impeded, for instance to make the discharge lamp suitable for a bipolar electrical power supply.

PRIOR ART

The fundamental physical events, technical properties and advantages as well as possible applications in or of discharge lamps for dielectrically impeded discharges are understood here to be known. The relevant literature can be referred to.

One essential performance characteristic for discharge lamps designed for dielectrically impeded discharges, that is, so-called "silent" discharge lamps, is the temporal and local homogeneity of the luminance. Special provisions for varying the distribution of the discharge in the discharge space have this as the goal, in particular individual localizable discharge structures, by means of special electrode structures that form preferential points for the discharge structures. Reference can be made for instance to German Patent Application DE 196 36 965 A1. By localizing the single discharges by means of electrode structures, optimized patterns in terms of the three-dimensional arrangement can be specified, which fill the discharge space in such a way that a favorable distribution of the luminance occurs. However, there is still a need for improvements to the temporal and local homogeneity of the luminance, above all in discharge lamps with significant length in at least one direction, such as barlike lamps with one direction of longitudinal extension, and flat lamps with two such directions.

SUMMARY OF THE INVENTION

The invention is thus based on the technical problem of disclosing a silent discharge lamp that is improved in terms of the temporal and local homogeneity of the luminance.

According to the invention, this problem is solved by a discharge lamp for dielectrically impeded discharges, having a discharge vessel filled with a discharge medium and having discharge electrodes which are at least partly separated from the discharge-medium by a dielectric layer, wherein the discharge vessel is elongated at least in a longitudinal direction, characterized by a thermal device for controlling the heat transport into and out of the lamp nonhomogeneously in the longitudinal direction, which is designed such that in operation, the temperature in the lamp is made homogeneous in the longitudinal direction.

The invention proceeds from the recognition that some nonhomogeneities in elongated silent discharge lamps occur only after time has elapsed in operation. It was possible to conclude that there was a relationship between the homogeneity of the temperature distribution in the discharge vessel and the homogeneity of the light projection. Evidently, since a homogeneously equally distributed pressure prevails in a discharge vessel, a nonhomogeneity in the temperature distribution results in a nonhomogeneous distribution of density of the discharge medium. The density of the discharge medium in turn has an effect on the physics of the discharge. In this sense, evidently a nonhomogeneity in the temperature resulting from the installation situation, the construction of the lamp itself, external temperature nonhomogeneities or other causes, is the cause of fluctuations in luminance over the at least one longitudinal direction in which the lamp extends.

In particular, it has been found that these variations in luminance can develop over the operating time, or in other words are generally linked via the purely local variation to a variation over time in the luminance distribution in the initial phase of operation. Thus the lack of temperature homogeneity is disadvantageous in two respects.

The general inventive concept is in the most general sense to exert influence on the temperature distribution by means of a thermal device, which controls the heat transport into and/or out of the lamp. According to the invention, this involves not simply a powerful cooling device, for instance, with which in a sense the attempt is made, by means of a suitably generous design of the cooling apparatus, to impress its temperature homogeneity on the lamps. Instead, the point of departure for the invention is that the thermal device in turn nonhomogeneously influences the heat transport, specifically in a way that is complementary to the intrinsic temperature behavior of the lamp. This is intended to counteract the development of the nonhomogeneous temperature profile in the discharge lamp.

In principle, the term "thermal device" used here covers any provisions by which influence can be exerted on the heat transport. In particular, it includes the control of the heat transport to the outside out of the lamp and in the opposite direction. Accordingly cooling devices in the most general sense can be considered, that is, devices that reinforce and improve heat dissipation from the discharge lamp to the outside, insulating devices, that is, devices that reduce the heat transport, which in general means heat transport from the discharge lamp to the outside, and finally also heating devices.

In very many cases, the intrinsic temperature behavior of the lamp, that is, the nonhomogeneous temperature profile that occurs without the thermal device of the invention, is characterized in that peripheral regions of the discharge lamp are not heated as much during operation as middle regions. This can be due for instance to the fact that the peripheral regions, referred to the portion of the discharge space assigned to them, have a larger surface area and thus greater heat losses. However, the invention also pertains to cases that are otherwise, for instance in which because of special mounting situations, the closeness of other components that produce heat, special discharge vessel geometries or otherwise, nonhomogeneous temperature profiles occur.

Concrete possibilities for thermal devices of the invention are for instance cooling bodies with cooling fins that are in thermal contact with the discharge lamp; the presence of the cooling fins, their length, or the density of their disposition is nonhomogeneous in a way that is adapted to the intrinsic temperature behavior of the discharge lamp. For instance, the cooling fins may either be present only in the middle of the lamp, or be located closer together in the middle of the lamp, or be stretched out with a larger surface area. Non-homogeneous cooling can also occur from a mounting device which in the middle region of the discharge lamp is coupled with good thermal conductivity, for instance, and acts as a cooling device by means of its own good thermal conductivity. This may for instance be a solid metal body. Naturally, both of these provisions may also be combined.

Another possibility is to insulate the peripheral regions of a discharge lamp thermally from the outside world, or else, by making thicker insulators or other components with insulating properties that are present anyway, such as discharge vessel walls, to provide for reinforced insulation in the peripheral region. For details of these various possibilities, see the exemplary embodiments in the further course of this description.

In the introductory part of the description, conventional provisions have already been mentioned with which influence can be exerted on the three-dimensional distribution of individual discharge structures. What is essential is that the provisions proposed with this invention and these conventional possibilities do not in any way preclude one another but instead prove to reinforce one another. In this sense, the invention is directed in particular to discharge lamps designed for the pulsed operating process developed by the present Applicant. This pulsed operating process assures the development of localizable individual discharge structures. For details, reference may be made to the prior art, and in particular to International Patent Disclosure WO94/23442. In particular, the invention is thus also directed to a discharge lamp, designed according to the invention, with a ballast device provided for the pulsed operating process.

One important application of silent discharge lamps is discharge lamps with an elongated barlike discharge vessel. In other words, they are elongated in only one longitudinal direction, and in the plane perpendicular to it are relatively small in cross section. Important applications of such "linear radiators " are in the field of office automation (OA), for instance. They can be used in scanners, such as in fax machines, electronic copiers, or in computer peripherals. They are equally suitable for conventional photocopiers. In this respect, it should be stated that the invention relates not only to discharge lamps that produce visible light but to UV radiators, for instance, as well.

In the field of these linear radiators, the invention is especially advantageous in relatively powerful linear radiators, in which experience tells that the disadvantages that are overcome or at least ameliorated by the invention occur to an increased extent. Powerful linear radiators can for instance have linear power densities of over 0.3 W/cm.

However, the invention is equally suitable for use in flat radiators, that is, large-area, essentially two-dimensionally extended discharge lamps, for instance for lighting liquid crystal screens from behind. In such flat radiators as well, greater cooling of a middle region relative to a peripheral region, or better insulation of the peripheral region from the middle region, or heating of the peripheral region is advantageous, that is, a thermal device along the lines of the invention. In principle, the possibilities already described can be chosen, such as cooling fins; the cooling fins are disposed correspondingly nonhomogeneously not only in the longitudinal direction but also in the transverse direction (that is, in the plane of the flat radiator). One example of this is a component part of the exemplary embodiments that will be described hereinafter.

Another possibility that is also illustrated in the exemplary embodiments has a generally flat metal sheet, which is in superficial thermal contact with the discharge vessel of the flat radiator. Recesses are provided in the metal sheet and define ribs that divide at least a middle region of the sheet from a peripheral region, and optionally also define a plurality of intermediate regions graduated from the middle region toward the peripheral region. The middle region of the metal sheet can be cooled by being embodied as a cooling device itself, for instance with cooling fins, or by being in thermal contact with a cooling device. The ribs make it possible to vary the heat transport from the peripheral region into the cooled middle region, so that once again, nonhomogeneous control of the heat transport out of the lamp into the metal sheet can be effected. The directly cooled middle region of the sheet will in fact cool the lamp more markedly than the outer region or regions joined to it only via the ribs.

BRIEF DESCRIPTION OF THE DRAWINGS

The invention is described in further detail below in terms of various exemplary embodiments. Characteristics disclosed can be essential to the invention both individually or in combinations other than those shown. Individually, the drawings show.

DETAILED DESCRIPTION OF THE DRAWINGS

Figure 1:
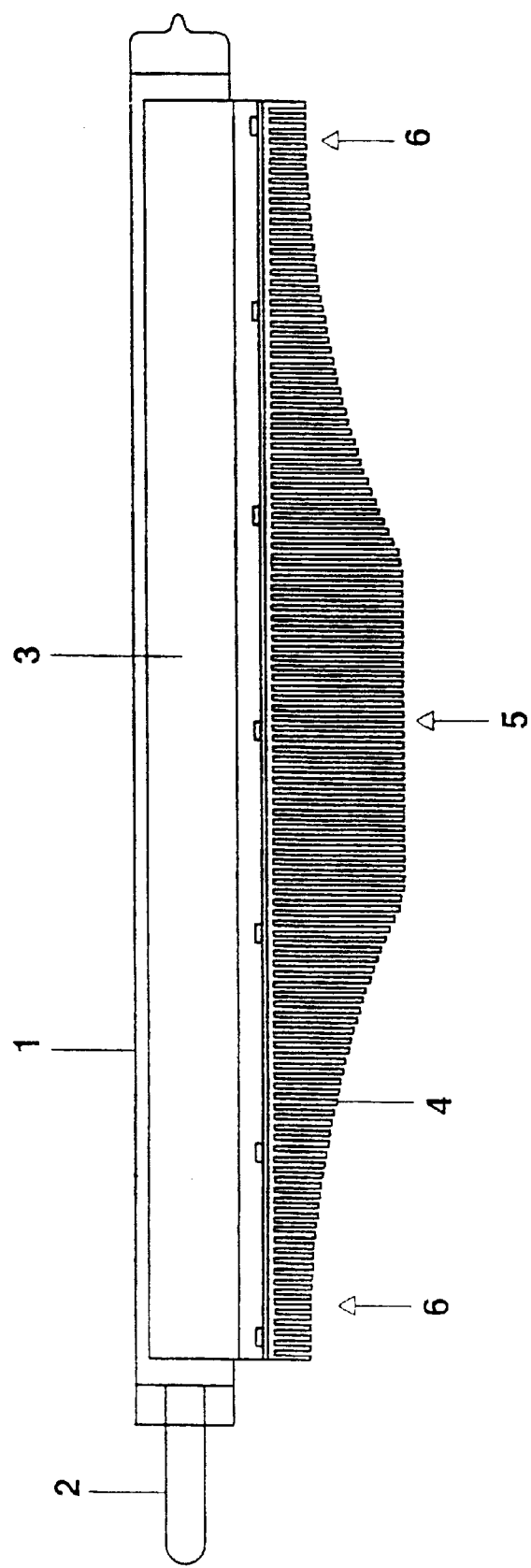
FIG. 1, a schematic view of a first exemplary embodiment of a discharge lamp of the invention.

FIG. 1, as the first exemplary embodiment, shows a silent discharge lamp according to the invention, which essentially comprises an elongated glass tube 1, closed on one end, which on its open end is closed by a suitable stopper 2. Details of this lamp with regard to the electrode structure, the luminous coating, and the like will not be provided here, because they are not essential to the invention. However, German Patent Disclosure DE 197 18 395 can be referred for further details. Naturally, instead of the internal electrodes shown in this reference, one or more external electrodes can be used.

In the longitudinal direction corresponding to the horizontal length in terms of FIG. 1, the most homogeneous possible luminance of the discharge lamp is to be attained. According to the invention, this is reinforced by a cooling body 3, which is joined thermally conductively to the lamp over practically the entire length of the lamp, or in other words rests over a large surface area on it or is clamped or glued to it. The cooling body 3 has many fins 4, forming cooling faces and oriented perpendicular to the longitudinal direction, which are staggered parallel to one another. The cooling fins 4 are relatively small in size in an outer peripheral region 6, in the vicinity of the left- and right-hand ends of the discharge lamp; that is, they protrude only a short distance from the base part, near the lamp, of the cooling body 3. In a middle region 5, which corresponds to the center of the lamp, the cooling fins 4 are conversely embodied very much longer and therefore exhibit a markedly greater cooling action. Between the middle region 5 and the peripheral region 6, smooth transitions in terms of the length of the cooling fin are provided.

Figure 2:
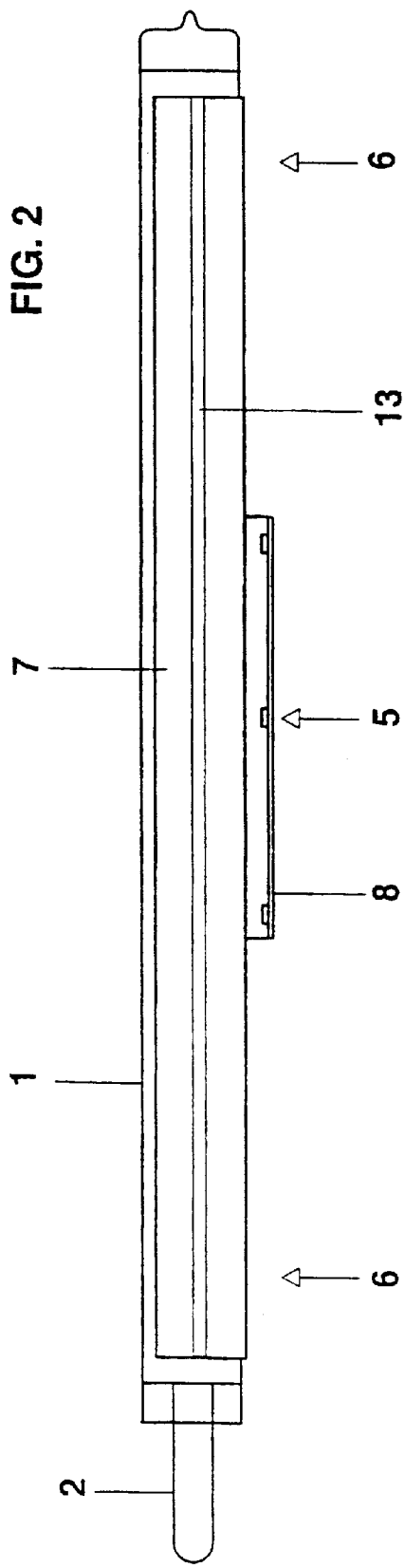
FIG. 2, a schematic view of a second exemplary embodiment of a discharge lamp of the invention.
Figure 3:
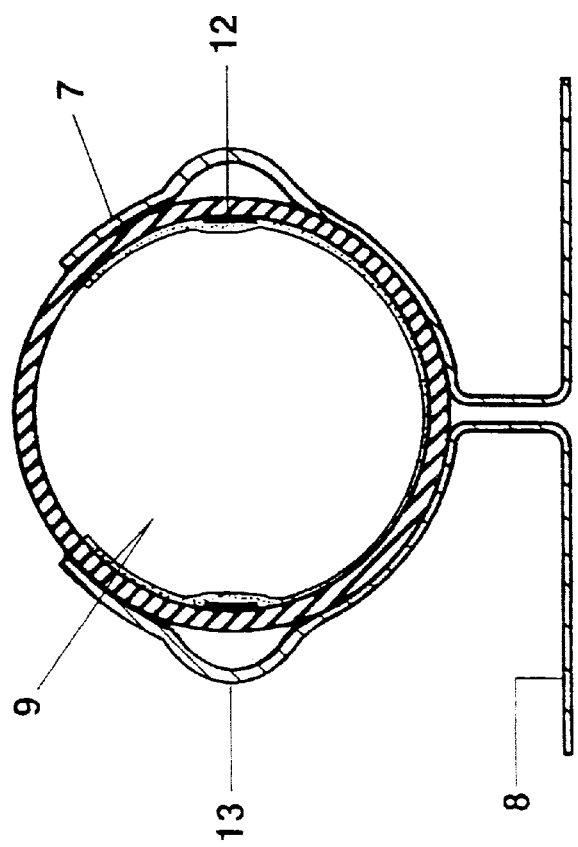
FIG. 3, a cross section through the discharge lamp of FIG. 2.

As an alternative to this, FIG. 2 shows a second exemplary embodiment, in which a discharge lamp, corresponding to the view in FIG. 1, is provided with a metal shell 7, which in turn is in good thermal contact with the discharge lamp. FIG. 3 shows a cross section through the view in FIG. 2, seen horizontally in terms of FIG. 2, specifically through the middle region 5 of FIG. 2. It can be seen that the metal shell 7 embraces the discharge lamp on both sides, with approximately the upper third of the discharge lamp, which is circular in cross section, remaining exposed so that it can emit light. Correspondingly, in the interior of the discharge lamp, a reflective layer 9 is provided in areas complementary to the surrounding shell 7; see DE 197 18 395, already cited.

In FIG. 3, it can be seen in cross section that between the reflective layer 9 and the glass tube 1, opposed electrode strips 12 are provided, which are symmetrical to the opening of the lamp in the upper third. At these points, there is a spacing between the shell 7 and the glass tube 1, within which spacing the shell 7 extends in a somewhat bulging form 13 in the region of the electrode strips 12, with spacing from the glass tube 1. Somewhat above and somewhat below the electrode strips 12, however, the shell 7 again contacts the glass tube 1. This structure has the advantage of a low capacitive coupling between the shell 7 and the electrode strips 12. It is not of essential significance to the thermal properties, since in the remaining region of the shell 7, there is good thermal contact with the lamp tube 1. The other exemplary embodiments can also have comparable structures, which is not shown in further detail.

In the middle region 5, the metal shell 7 has a foot 8, which in turn is mounted with good thermal conductivity on a base of no further interest here, which however can act as a heat sink or heat buffer. As a result, in the middle region 5, the foot 8 carries heat to a greater extent out of the shell 7 and thus out of the discharge lamp than is the case in the peripheral region 6, where there is no foot. The shell 7 with the foot 8 in the middle region 5 thus forms a cooling device with nonhomogeneous action along the horizontal length of the discharge lamp, as is also the case in the first exemplary embodiment.

Figure 4:
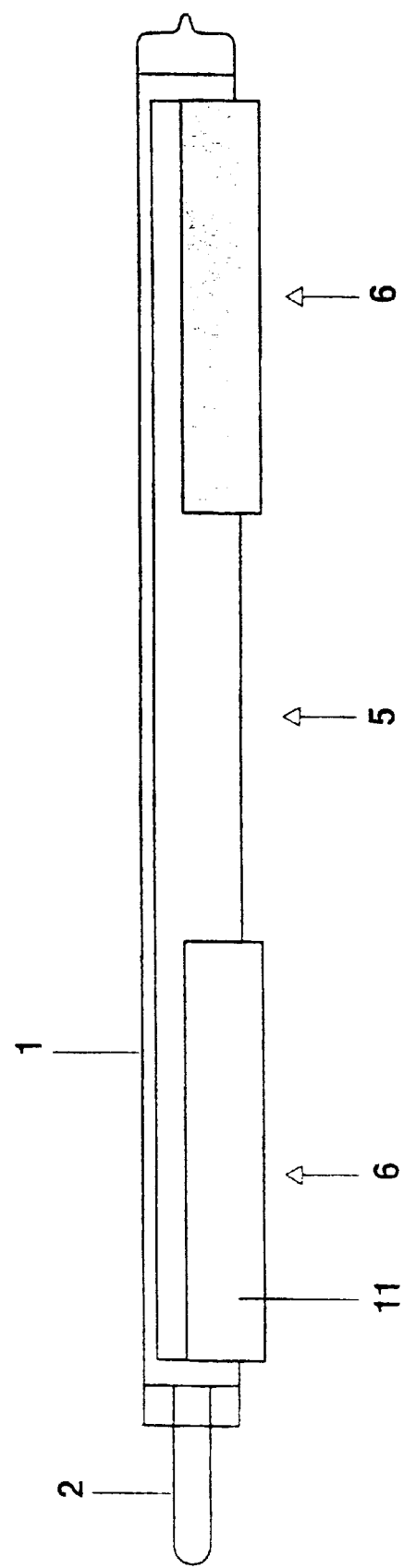
FIG. 4, a schematic view of a third exemplary embodiment of a discharge lamp of the invention.
Figure 5:
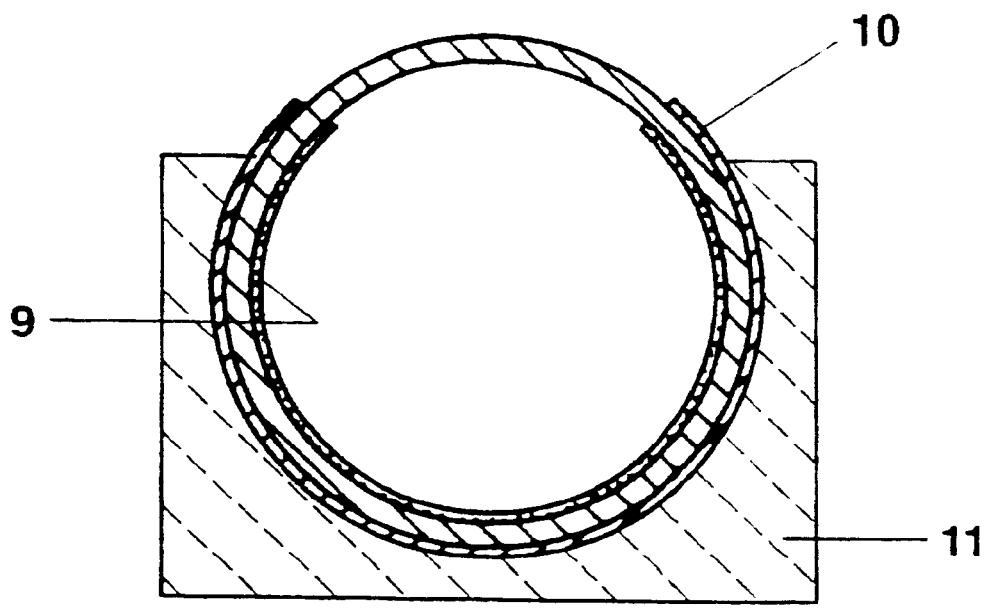
FIG. 5, a cross section through the discharge lamp of FIG. 4 in the peripheral region.
Figure 6:
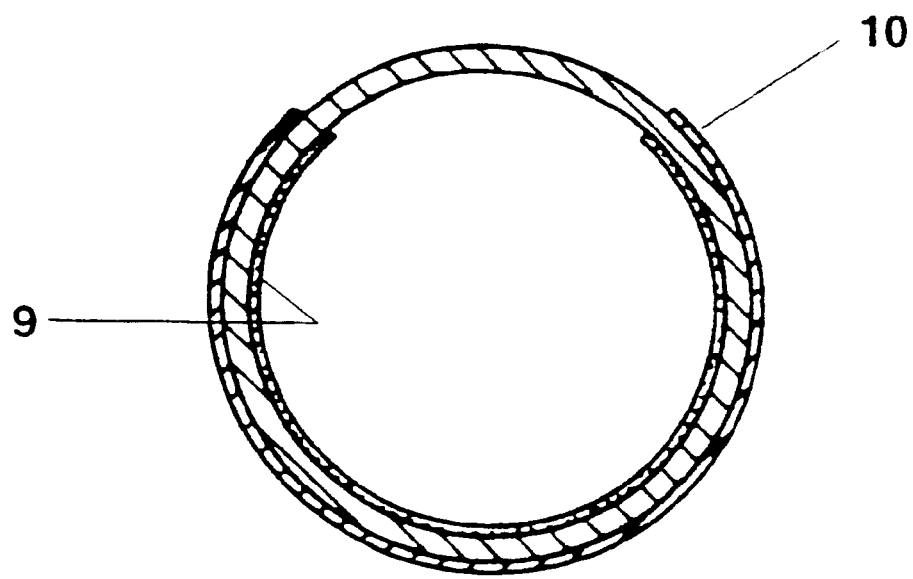
FIG. 6, a cross section through the discharge lamp of FIG. 4 in the middle region.

FIGS. 4, 5 and 6 show a further example. FIG. 5 shows a section corresponding to FIG. 3 in perspective, but through a peripheral region 6 of FIG. 4, while conversely FIG. 6 shows a corresponding section through the middle region 5. It can be seen that once again, a metal shell 10 is provided which is in good thermal contact with the discharge lamp, but in this case does not act as a cooling device but only as a shield against the electromagnetic radiation from the discharge lamp. This function is furthermore intrinsic to the metal shell 7 of FIG. 2 as well. In both cases, the shells 7 and 10 are preferably grounded for that purpose. In the third exemplary embodiment shown in FIG. 4, however, an additional thermal insulation 11 is provided around the shell 10 in the peripheral region 6, so that the middle region 5 can better dissipate the heat loss from the discharge to the outside than the peripheral region 6 can. This third exemplary embodiment accordingly shows a corresponding thermal device, in the sense of a nonhomogeneous insulation of the discharge lamp in the longitudinal direction.

Naturally the versions shown in the various exemplary embodiments can also be combined; for instance, an insulation in the third exemplary embodiment can be combined with cooling in accordance with the first or second exemplary embodiment. It is a common feature of all three cases that the temperature homogeneity is markedly improved in the longitudinal direction of the linear radiator. Because the gas density inside the discharge lamp is largely homogeneous given the equal temperature and largely homogeneous temperature, a very homogeneous distribution of luminance is thus achieved as well.

Figure 7:
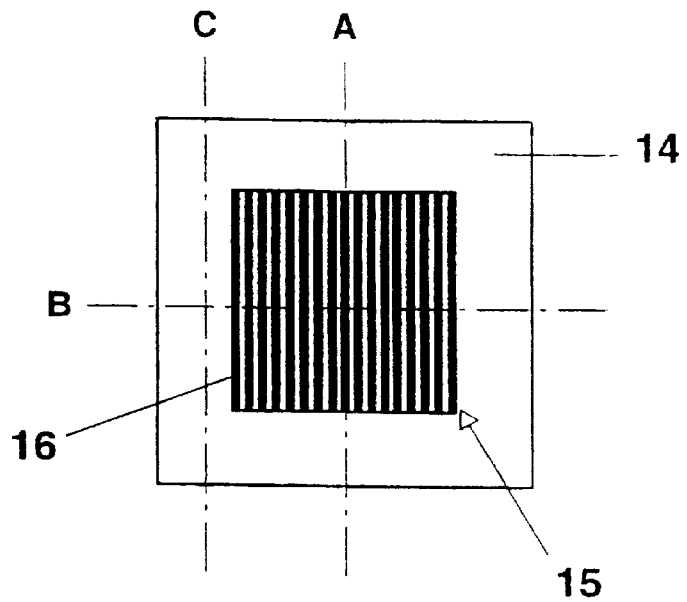
FIG. 7, a schematic view of a fourth exemplary embodiment, namely a flat radiator according to the invention.

FIG. 7 schematically shows an exemplary embodiment in the form of a flat radiator 14. The flat radiator 14 is shown here only as a flat, two-dimensionally extended plate, because its technical details are familiar to one skilled in the art from the prior art. Reference may be made for instance to International Patent Disclosure WO98/43276.

Figure 8A:
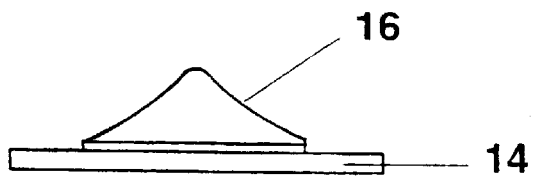
FIGS. 8A, 8B, 8C, sectional views through the exemplary embodiment of FIG. 7.
Figure 8B:
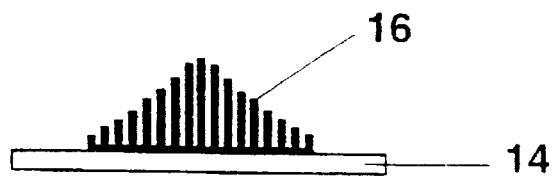
Figure 8C:
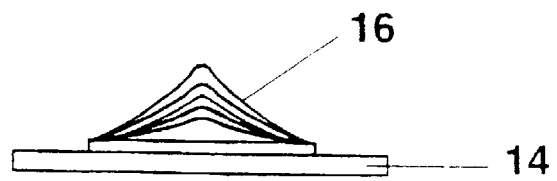

A cooling body 15 is mounted on the flat radiator 14, on the side opposite the light emission side, and covers the middle region of the flat radiator. FIGS. 8A, 8B, 8C show a section as indicated in FIG. 7, along the lines A, B and C, respectively (with a side view of the cooling body 15), through the flat radiator 14 and the cooling body 15 of FIG. 7. It can be seen that as in the exemplary embodiments of FIG. 1, the cooling body has cooling fins 16, extending parallel to and spaced apart from one another. The cooling fins 16 are designed such that they are highest in the middle region of the cooling body 15. To that end, they have a profile that extends upward from both ends to a maximum height in the middle; the maximum heights of the cooling fins in the middle are staggered in such a way that the profile of an individual cooling fin 16 in FIG. 8A essentially corresponds to an envelope over the maximum heights, visible in FIG. 8B, of the entire number of cooling fins 16. The overall result thus, as a result of the design of the cooling fins 16 and the central disposition of the cooling body 15 that does not reach the periphery, is a nonhomogeneity of the cooling action with its focal point in the middle of the flat radiator 14.

Figure 9:
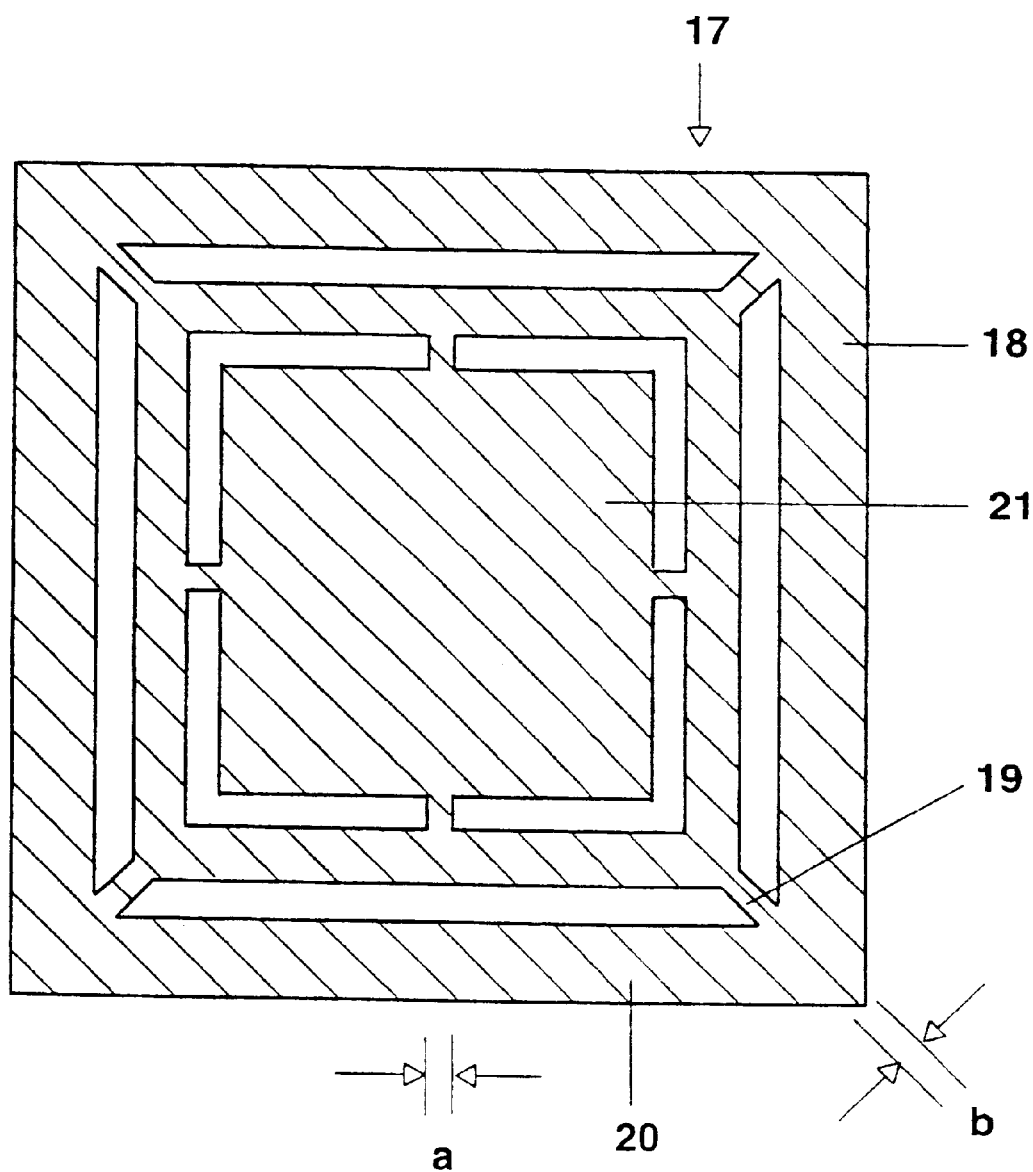
FIG. 9, a fifth exemplary embodiment in the form of a flat radiator.

Finally, FIG. 9 shows a final exemplary embodiment, which also pertains to a flat radiator. The flat radiator is shown only schematically and is identified overall by reference numeral 17. A metal sheet 18, largely corresponding to the area of a discharge vessel, not shown in further detail, is in good superficial thermal contact with the discharge vessel of the flat radiator 17 and has recesses shown in further detail in FIG. 9. The recesses form various ribs 19, which connect a middle region 21 of the metal sheet 18 to a peripheral region 20. In FIG. 9, an intermediate region is also provided between the middle region 21 and the peripheral region 20, but it is not absolutely necessary. By means of one or more such intermediate regions, the nonhomogeneity of the thermal influence on the discharge lamp can be made more uniform.

The middle region 21 is in contact with a cooling device, not further shown, such as cooling fins. By means of the heat transport, limited by the ribbed form of the metal sheet 18, between the middle region 21 and the peripheral region 20, the middle region 21 is thus cooled very much more markedly than the only indirectly cooled peripheral region 20. The intermediate region naturally assumes an intermediate position in terms of cooling.

Control of this heat transport can follow by means of the number and the length, represented by a and b in FIG. 9, of the ribs.

This embodiment, like the others, can perform a function to shield against electromagnetic radiation from the lamp or can be combined with the shielding.

In the exemplary embodiments shown here, no relevant dependence of the luminance on the temperature is demonstrated, as long as the temperature variations are within the typical range of a few tens of Kelvins. In fact, thermal energies result but are not significant in comparison to the definitive energies for the physics of the discharge. As long as creating a nonhomogeneity of the gas density does not lead to any heterogeneous discharge situation, not only can the local homogeneity be improved as a result, but the startup behavior over time can be practically avoided.

In the linear radiators shown here in particular, it is furthermore possible, depending on the operating position, that is, above all in vertical operation with an additional vertical temperature nonhomogeneity, for a situation to arise in which, without the invention, the ignition conditions inside a powerful elongated linear radiator would become so nonhomogeneous that the discharges would burn only in the regions of lower gas density and thus over long free distances. Since the heat loss is also concentrated in these regions, this mechanism has a self-reinforcing character. The invention offers effective aid against it.

What is claimed is:

1. A discharge lamp for dielectrically impeded discharges, having a discharge vessel (1, 2) filled with a discharge medium and having discharge electrodes which are at least partly separated from the discharge medium by a dielectric layer,
   wherein the discharge vessel (1, 2) is elongated at least in a longitudinal direction,
   characterized by a thermal device (3, 4, 7, 8, 10, 11) for controlling the heat transport into and out of the lamp nonhomogeneously in the longitudinal direction,
   which is designed such that in operation, the temperature in the lamp is made homogeneous in the longitudinal direction.

2. The discharge lamp of claim 1, in which the nonhomogeneity distinguishes a middle region (5) of the discharge lamp from a peripheral region (6).

3. The discharge lamp of claim 1, in which the thermal device (3, 4, 7, 8, 10, 11) has a cooling device (3, 4, 7, 8).

4. The discharge lamp of claim 3, in which cooling fins (4) are provided, which are disposed nonhomogeneously in the longitudinal direction in terms of their presence, their length and/or their density.

5. The discharge lamp of claim 2, having a mounting device (8), which is coupled to the middle region (5) in a manner providing good thermal conductivity.

6. The discharge lamp of claim 1, in which the thermal device (10, 11) has an insulating device (11).

7. The discharge lamp of claim 2, in which the peripheral region (6) is thermally insulated.

8. The discharge lamp of claim 1, in which the thermal device has a heating device.

9. The discharge lamp of claim 1, having a ballast device designed for a pulsed operating process.

10. The discharge lamp of claim 1, in which the discharge electrodes have structures for defining the location of individual discharges.

11. The discharge lamp of claim 1, in which the discharge vessel (1, 2) is elongated in barlike form.

12. The discharge lamp of claim 11, which is designed for a linear power density in the longitudinal direction of 0.3 W/cm or more.

13. The discharge lamp of claim 11, which is designed for a photocopier or a scanner.

14. The discharge lamp of claim 1, which is embodied as a flat radiator (14, 17).

15. The discharge lamp of claim 14, in which a metal sheet (18) that is in superficial thermal contact with the discharge vessel has recesses that define ribs (19), and a middle region (21) connected to a peripheral region (20) of the metal sheet (18) via the ribs (19) has a cooling device or is connected to a cooling device.

16. The discharge lamp of claim 4, in which the discharge vessel (1, 2) is elongated in barlike form.

* * * * *